United States Patent
Simpkins et al.

(10) Patent No.: US 6,172,088 B1
(45) Date of Patent: Jan. 9, 2001

(54) TESTOSTERONE COMPOUNDS AND USE FOR THE PROTECTION OF NEURONS

(75) Inventors: James W. Simpkins, Gainesville, FL (US); Katherine D. Gordon, Winchester; Robert Leonard, Swampscott, both of MA (US)

(73) Assignees: University of Florida Research Foundation, Inc., Gainesville, FL (US); Apollo Biopharmaceutics, Inc., Cambridge, MA (US)

(*) Notice: Under 35 U.S.C. 154(b), the term of this patent shall be extended for 0 days.

(21) Appl. No.: 09/198,416

(22) Filed: Nov. 24, 1998

Related U.S. Application Data

(60) Provisional application No. 60/066,694, filed on Nov. 24, 1997.

(51) Int. Cl.$^7$ .......................... A61K 31/44; A61K 31/56
(52) U.S. Cl. .......................... 514/340; 514/181; 514/182
(58) Field of Search .................. 514/340, 181, 514/182

(56) References Cited

U.S. PATENT DOCUMENTS

| | | | |
|---|---|---|---|
| 4,897,389 | 1/1990 | Aroonsakul | 514/171 |
| 5,453,428 | 9/1995 | Kaminski | 514/279 |

FOREIGN PATENT DOCUMENTS

| | | |
|---|---|---|
| 61 K 31/40 | 1/1995 | (DE) . |
| 0 679 642 | * 11/1995 | (EP) . |
| 0 679 642 A1 | 11/1995 | (EP) . |
| 0 792 642 | * 9/1997 | (EP) . |
| 0 792 642 A1 | 11/1997 | (EP) . |
| WO94/24146 | 10/1994 | (WO) . |

OTHER PUBLICATIONS

Rich et al. Mov. Disord. 9(3): 353–357, 1994.*
Bishop, et al., *Molecular and Cellular Neuroscience*, (1994), vol. 5, pp. 303–308.
Georgiou et al., *Movement Disorders*, (1995), vol. 10, No. 4, pp. 472–481.
Goodman, et al., *J. Neurochem*, (1996), vol. 66, pp. 1836–1844.
Green, et al., *J. Neuroscience*, (1997), vol. 17, pp. 511–515.
Matsuda, et al., *Amer J. Physiologic.*, (1994), vol. 267, pp. H887–H893.
Menzies, et al, *Neurosurgery*, (1992), vol. 31, pp. 100–106.
Nakao, et al., *Atherosclerosis*, (1981), vol. 39, pp. 203–209.
Rich and Ovsiew, *Movement Disorders*, (1994), vol. 9, No. 3, pp. 353–357.
Rosenblum, et al. *Thromb. Res.*, (1987), vol. 45, pp.719–728.
Schor, et al., *Euro J. Clin. Inves.*, (1994), vol. 24 Supp., pp. 50–52.
Simpkins, et al., *Neurobiology of Aging*, (1994), pp. S195–S197.
Singer, et al., *Neurosci. Let.*, (1996), vol. 212, pp. 13–16.
Singh, et al., *Brain Res.*, (1994), vol. 644, pp. 305–312.
Uzunova, et al., *Prostaglandins*, (1977), vol. 13, pp. 995–1002.
Toung et al., *Stroke*, (1998), vol. 29, pp. 1666–1670.
Zukowska–Grojec, Ann, *N.Y. Acad. Sci.*, (1995), vol. 771, pp. 219–233.

* cited by examiner

*Primary Examiner*—James O. Wilson
*Assistant Examiner*—Howard Owens
(74) *Attorney, Agent, or Firm*—Bromberg & Sunstein LLP

(57) ABSTRACT

Androgens and their derivates and analogs, such as anabolic agents, are characterized by at least one substituent or substituent grouping with radical trapping properties. These compounds are used as androgen or anabolic agent substitutes or therapeutical agents for treating androgen defficiency; for treating benign prostate hypertrophy and prostate carcinome, in particular with a testosterone-based compound; for treating osteoporosis, in particular post-menopausal osteoporosis in women, preferably associated with estrogen and/or gestagens; for treating brain oedema induced by vasculary or ischemic troubles, subarachnoidal bleeding, ischemic shock and cerebral insult; for treating asthma in its various forms, for treating Alzheimer's disease, Parkinson's disease; for organ transplants; and for treating androgen-dependent and non androgen-dependent malign neoplasia

5 Claims, 3 Drawing Sheets

TESTOSTERONE COMPOUNDS AND USE FOR THE PROTECTION OF NEURONS

CROSS REFERENCE

The application gains priority from the provisional application serial number 60/066,694 filed Nov. 24, 1997, herein incorporated by reference.

TECHNICAL FIELD

The present invention relates to novel methods for conferring neuroprotection on a subject that relies on administering an effective dose of at least one testosterone inhibitor.

BACKGROUND TO THE INVENTION

Neurodegenerative diseases have a major impact on society. For example, approximately 3 to 4 million Americans are afflicted with a chronic neurodegenerative disease known as Alzheimer's disease. Other examples of chronic neurodegenerative diseases include diabetic peripheral neuropathy, multiple sclerosis, amyotrophic lateral sclerosis, Huntingdon's disease and Parkinson's disease. Not all neurodegenerative diseases are chronic. Some acute conditions arise from stroke, schizophrenia, cerebral ischemia resulting from surgery and epilepsy as well as hypoglycemia and trauma resulting in injury of the brain, peripheral nerves or spinal cord. There is a need for improved therapeutic agents and methods for reversing or retarding neuronal damage associated with each of these conditions.

Neurodegenerative diseases and aging are characterized by a wide range of symptoms which vary in severity and range from individual to individual. For example, Alzheimer's disease is characterized by symptoms such as depression, aggression, impairment in short-term memory, impairment in intellectual ability, agitation, irritability and restlessness.

A common feature of neurodegenerative disorders and the process of aging in animals is the progressive cell damage of neurons within the central nervous system (CNS) leading to loss of neuronal activity and cell death. This loss of activity has been correlated with adverse behavioral symptoms including memory loss and cognitive deficits. Therapeutic agents that have been developed to retard loss of neuronal activity either have toxic side effects or are prevented from reaching their target site because of their inability to cross the blood-brain barrier. The blood-brain barrier is a complex of morphological and enzymatic components that retards the passage of both large and charged small molecules thereby limiting access to cells of the brain. There is a need for novel therapeutic agents that are readily transported across the blood-brain barrier as well as for novel methods of treatment of neurodegenerative disorders that directly target the damaged site and are non-toxic.

Traditional methods of treating neurological symptoms focus on: modifying the electrical impulse itself as it moves between and along neurons; or modifying the release or degradation of neurotransmitters. It is now recognized that neuronal cell density has an important impact on function. In various pathological conditions, loss of cell density has been observed resulting from accelerated neuronal cell death. The pattern of degeneration of neurons typically originates from the nerve terminals and progresses "backward" toward the cell body (retrograde degeneration). In several systems, lesioning of certain brain regions results in compensatory sprouting of axons. This plasticity of neurons is attributed at least in part to the presence of trophic growth factors.

These findings have spurred efforts to identify therapeutic agents that compensate for cell loss by stimulating sprouting of dendrites and axons of remaining cells so as to improve the structural integrity of the damaged region. However, the optimal density of neurons and neuronal extensions is a delicate balance between deficiency and excess, a balance that varies with the environment of the cells. This balance can be disrupted when therapeutic agents act on normal or inappropriate tissue. There is a need therefore to target therapeutic agents at a therapeutic dose specifically to those regions where they are required, or, alternatively, to identify agents that have a natural specificity for the target site only, or that are effective at nontoxic doses.

Neurotrophic factors that promote growth and maintenance of cells of the central nervous system (CNS) and sympathetic and sensory neurons of the peripheral nervous system have been investigated for use as therapeutic agents. In particular, the administration of nerve growth factor (NGF), a protein which is normally transported retrogradely in the intact brain from the hippocampus to the septal cholinergic cell bodies as well as from the cortex to the nucleus basalis, provides trophic support to cholinergic neurons and has been shown in animal models to have utility in reducing the effects of neurodegeneration due to trauma, disease or aging. One of the major problems confronting the use of NGF as a therapeutic agent is finding an appropriate method of increasing the levels of NGF at the appropriate target site. NGF is a large molecule and as such cannot normally pass across the blood-brain barrier and therefore has very limited access to the cells of the brain. Current methods for administering nerve growth factor across the blood-brain barrier include: polymeric implants, osmotic minipumps, cell therapy using genetically engineered autologous or heterologous cells secreting NGF for implantation into the brain, and methods of increasing the permeability of the blood-brain barrier thereby allowing diffusion of these molecules to cells in the brain. Where exogenous NGF is used, a relatively large amount of relatively costly recombinant protein is required. Non-localized targeting not only decreases the amount of protein available at the target site but also results in stimulation of growth of neurons at inappropriate sites resulting in potential harmful effects for the subject.

An additional approach to treating neurological symptoms has followed the observation that certain amino acids (glutamic acid and aspartic acid) act as excitatory neurotransmitters that bind the N-methyl D-aspartate (NMDA) receptor. Excess release of these amino acids (EAA) causes overstimulation of the neurons in neurodegenerative diseases as well as in conditions of hypoglycemia or trauma, resulting in neuronal loss and behavioral dysfunctions. NMDA is a potent and toxic analogue of glutamate which has been shown in animal studies to mediate much of the neuronal death associated with head trauma, hypoglycemia, anoxia, hypoxia and other conditions, and compromises the flow of blood, oxygen or glucose to the central nervous system.

A number of synthetic compounds that act as antagonists of the receptor have been described and tested in animal models. The possibility that these compounds are toxic in humans remains unresolved. Despite many years of clinical research, these antagonists are not as yet available as therapeutic products for treating patients.

Estrogen compounds have been found to have a neuroprotective effect (Simpkins et al., U.S. Pat. No. 5,554,601 herein incorporated by reference). Furthermore, the class of compounds identified as four ring cyclopentanophenanthrene compounds have been shown to have a neuroprotective effect. (Simpkins et al., U.S. Ser. No. 08/685,574, herein incorporated by reference). These observations have been confirmed in a variety of in vitro and in vivo models for neurodegeneration [C. Behl, et al., *Biochem. Biophys. Res. Comm.*, Vol. 216, (1995), pp. 473–482; J. Bishop, et al., *Molecular and Cellular Neuroscience*, Vol. 5, (1994), pp. 303–308; Y. Goodman, et al., *J Neurochem*, Vol. 66, (1996), pp. 1836–1844; P. S. Green, et al., *J Neuroscience*, Vol. 17, (1997), pp. 511–515; J. W. Simpkins, et al., *Neurobiology of Aging*, Vol. 15, (1994), pp. S195–S197; C. A. Singer, et al., *Neurosci. Let.*, Vol. 212, (1996), pp. 13–161].

There is a continued need to identify neuroprotective agents to retard neuron loss that plays a significant role in disease progression in neurodegenerative diseases as well as trauma and aging.

SUMMARY OF THE INVENTION

A method is provided for conferring neuroprotection on a population of cells in a subject that includes in a preferred embodiment, the steps of providing an effective dose of a non-estrogen inhibitor of testosterone metabolism in a pharmaceutical formulation, wherein the inhibitor further excludes four ring cyclopentanophenanthrene compounds; and administering the inhibitor to the subject so as to confer neuroprotection. In a preferred embodiment, the subject is a male subject.

In a preferred embodiment, the method further includes an inhibitor of testosterone metabolism that is selected from the group consisting of: a hormone, a steroidal anti-androgen, a non-steroidal anti-androgen, an androgen synthesis inhibitor, a luteinising hormone receptor antagonist, a luteinising hormone receptor agonist and a 5-alpha-reductase inhibitor, the compound being preferably administered by a route selected from oral, intramuscular, transdermal, buccal, intravenous and subcutaneous.

In a further embodiment of the invention, a method of conferring neuroprotection on a population of cells in a subject is provided that includes the steps of providing a mixture containing a plurality of non-estrogen inhibitors of testosterone metabolism at an effective dose and in a pharmaceutical formulation, wherein the inhibitor further excludes four ring cyclopentanophenanthrene compounds; and administering the inhibitor to the subject so as to confer neuroprotection.

In a further embodiment of the invention, a method of treating a neurodegenerative disorder in a subject, includes providing an effective dose of a non-estrogen inhibitor of testosterone metabolism in a pharmaceutical formulation wherein the inhibitor further excludes four ring cyclopentanophenanthrene compounds; and administering the formulation to the subject so as to retard the adverse effects of the disorder.

DETAILED DESCRIPTION OF THE INVENTION

Figure 1:
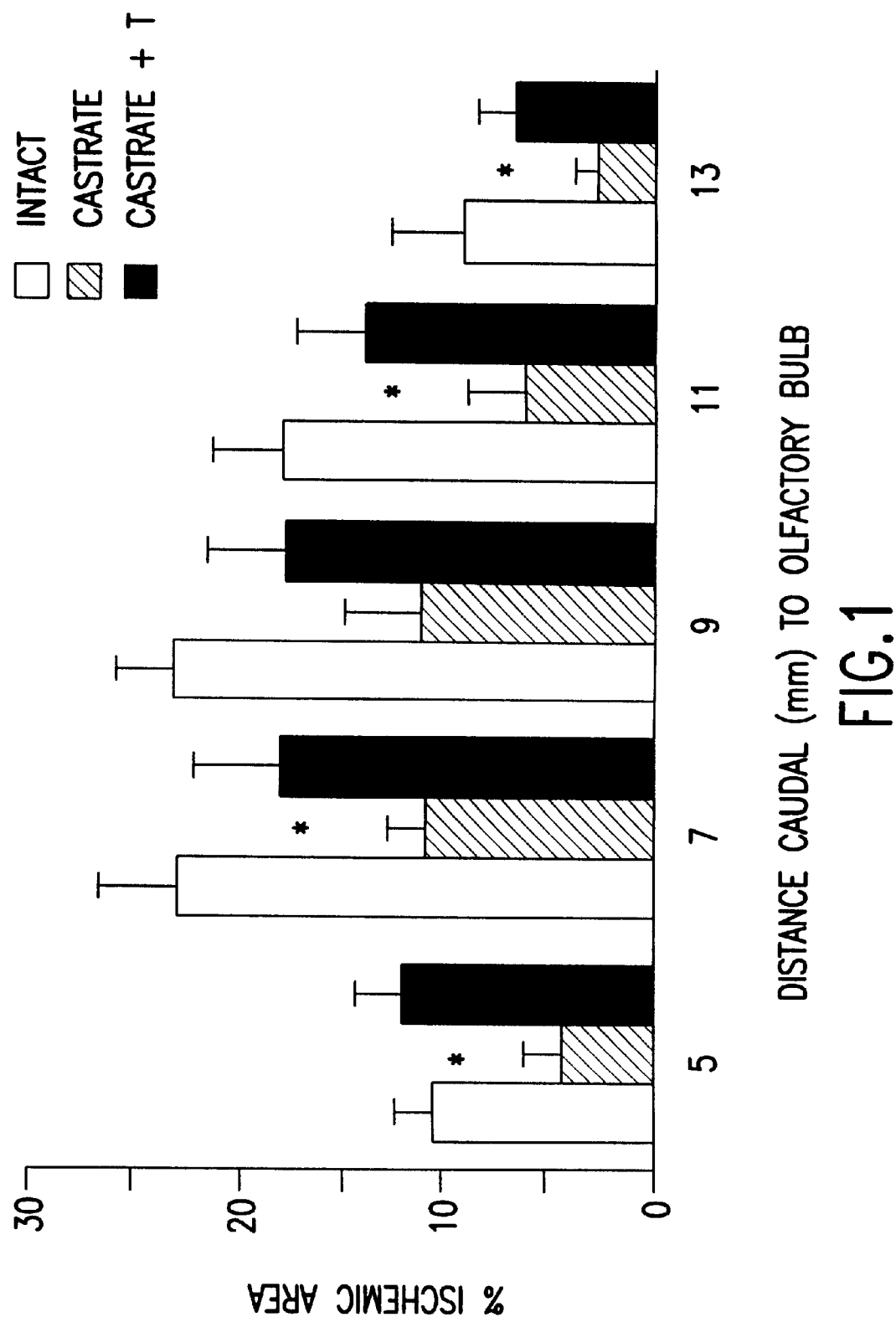
FIG. 1 shows the effects of androgen environment on ischemic lesion size in male rats. Depicted are the percentage of the cross-sectional areas of the brain (mean percent ischemic area±SEM) in various slices taken at increasing distances caudal to the olfactory bulb from gonad intact (Intact), castrated (Castrate) and castrated animals with testosterone replacement (Castrate+T). * indicates p<0.05 versus intact rats for individual brain sections.

Neuron loss is associated with disease progression and therefore methods to retard neuron loss are desirable for disease management. Whereas certain classes of compounds have shown efficacy in retarding neuron loss, it is desirable to identify additional compounds that may prove effective at retarding neurodegenerative disease progression and aging as well as the sequelac of trauma. In aging populations, there is a particular need for methods of protecting neurons from cell death caused by neurodegenerative diseases, aging and trauma.

While estrogens have been found to have neuroprotective properties (Simpkins et al., 1996). little is known about the action of the male counterpart—testosterone with regard to neuroprotection.

Testosterone enhances the release of the vasoconstrictor substance, neuropeptide Y, in response to stress [Z. Sukowska-Grnjec, Ann, *N. Y. Acad. Sci.*, Vol. 771, (1995), pp. 219–33]. Additionally, testosterone has been shown to inhibit synthesis of the vasodilator, protacyclin, in aortic tissue [J. Nakao, et al., *Atherosclerosis*, Vol. 39, (1981), pp. 203–209], to enhance thromboxane A2-induced constriction of coronary arteries [K. Schor, et al., *Euro. J. Clin. Inves.*, Vol. 24 Supp., (1994), pp. 50–52], and to reduce thromboxane A2 receptors in aorta [K. Matsuda, et al., *Amer. J. Physiologic.*, Vol. 267, (1994), pp. H887–H893]. Testosterone has also been shown to enhance platelet aggregation [W. I. Rosenblum, et al., *Thromb. Res.*, Vol. 45, (1987), pp. 719–728]and arachidonic acid-induced thrombosis [A. D. Uzunova, et al., *Prostaglandins*, Vol. 13, (1977), pp. 995–1002].

Aroonsakul specifically included testosterone in a mixture for treating symptoms of patients with Alzheimer's disease, suggesting that testosterone might have a beneficial effect as a therapeutic agent. (Aroonsakul (1990) U.S. Pat. No. 4,897, 389). However, others have reported that endogenous testosterone does not diminish or enhance neuron survival in male rats with middle cerebral artery occlusion (MCAO) (Toung et al. *Stroke*, 1998: 29:1666–1670).

In contrast to the foregoing, it is here demonstrated for the first time that testosterone has an adverse effect on retardation of neuron loss (see Examples). Consequently, this observation provides for the use of testosterone inhibitors to reverse the negative effect of testosterone on neuron loss so as to enhance neuroprotection. Testosterone inhibitors known in the art include compounds for treating prostate cancer. In a preferred embodiment of the invention, a new use is provided for these compounds and other testosterone inhibitors as defined below.

According to the invention, testosterone inhibitors may be used singly or in combination to prevent neuron loss which occurs following an injury or disease. Testosterone inhibitors may be used to treat neuron loss in conditions that include but are not limited to: stroke, transient ischemic events, subarrachinoid hemorrhage, neuron loss secondary to cardiac or neural surgery, shock, head trauma, Alzheimer's disease, Parkinson's disease, Huntingdon's disease, AIDS, dementia, aging and schizophrenia.

"Testosterone inhibitors" are defined here and in the claims as compounds which decrease the concentration or activity of testosterone or inactivate or otherwise antagonize or inhibit the activity or metabolism of testosterone which would otherwise lead to neuron loss. According to the definition, this class of compounds does not include four ring cyclopentanophenanthrene compounds or estrogen compounds. The testosterone inhibitor molecules include antagonists and agonists of testosterone that counteract the action of testosterone. Without wishing to be limited to scientific theories, testosterone inhibitors used in the invention, may act for example by binding to the androgen receptor, interfering with nuclear accumulation of active receptor-hormone complexes, by down-regulating the synthesis testosterone or acting on the metabolism of testosterone. The testosterone inhibitor molecules used according to the invention may include compounds found to be effective in treating prostrate cancer. Testosterone inhibitors are not limited to but are exemplified by: (1) Hormones which inhibit hypothalamic release of gonadotrophin releasing hormone (GnRH); (2) GnRH analogues (e.g., goserelin Zoladex), leuprorelin (Prostap), buserelin (Suprelfact), triptorelin (De-capeptyl), (nafarelin); (3) steroidal anti-androgens (eg., cytoproterone acetate, megestrol acetate); (4) pure anti-androgens (eg., flutamide (Drogenil), nilutamide, bicalutamide (Cadodex); (5) androgen synthesis inhibitors (eg., ketoconazole); (6) 5-alpha-reductase inhibitors, e.g., finasteroid or Proscen and including inhibitors for treating prostate cancer; (7) androgen receptor antagonists including cytoproterone, flutamide, cymetidine, ranitidine and spironolactone; (8) agonists and antagonists of the luteinizing hormone releasing hormone (LHRH).

"Estrogen compounds" are defined here and in the claims according to U.S. Pat. No. 5,554,601.

"Polycyclic phenolic compounds" are defined here and in the claims by the compounds enumerated in Simpkins et al. U.S. Ser. No. 08/685,574, herein incorporated by reference.

A preferred embodiment of the current invention is directed to the observation that the amounts of testosterone in a male animal is correlated with the extent of ischemic damage following a stroke. The correlation of testosterone as a negative risk factor in the outcome of cerebrovascular ischemia demonstrated in the accompanying example, is novel.

The data shows that plasma testosterone concentrations are highly correlated with increased ischemic brain damage from middle cerebral artery occlusion. The data is obtained using a rat model in which middle cerebral artery (MCA) occlusion has been used to produce focal ischemic lesions in the rat. This model is the preferred experimental model for studying neuron loss in the human brain. Reduction in plasma testosterone in the experimental MCA rat model, either through castration or treatment with estradiol, is associated with approximately a 50% reduction in ischemic lesion size.

The lesions produced by the MCA occlusion in male rats occurred in the frontal and parietal cortex and the basal ganglia, with the maximal extent of the lesion seen at 7 and 9 mm posterior to the olfactory bulb. Reduced ischemic damage was further detected in the rostral and caudal to these areas, where the anterior and posterior cerebral arteries, respectively, also supply the tissue [S. A. Menzies, et al, *Neurosurgery*, Vol. 31, (1992), pp. 100–106]. The brain samples taken from the expected region of the MCA lesion in control rats demonstrated the expected effects of the MCA occlusion. In sample rats that had been castrated, the castration resulted in a reduction of the size of the ischemic lesion by 59%. Testosterone replacement restored lesion size to the extent expected from the levels of plasma testosterone following replacement therapy. A strong positive relationship between plasma testosterone levels and lesion size was observed with a $r^2$ value of 0.922. These data suggest that regardless of other endocrine factors, plasma testosterone is a primary determinant of the size of ischemic lesions following MCA occlusion in the male rat. In female rats, ovariectomy enhances and estrogen treatment reduces by about 50% ischemic lesion following MCA occlusion [Simpkins, Ser. No. 08/749,703, incorporated by reference]. In the example, 17β-estradiol exerted a profound protective effect in intact male rats that were associated with a marked reduction in plasma testosterone concentrations. In the presence of testosterone from a Silastic® implant, estradiol was only partially effective in reducing lesion size.

TABLE 1

Effects of Gonadal Steroid Modification on Mortality and Plasma Testosterone Concentration Following Middle Cerebral Artery Occlusion.

| Treatment Group | N | Plasma Testosterone ng/ml mean ± sem | Mortality (%) |
|---|---|---|---|
| 1. Intact | 5 | 1.57 + 0.41* | 46 |
| 2. Castrate | 8 | 0.07 + 0.03 | 15 |
| 3. Castrate + T | 11 | 0.67 + 0.07** | 12 |
| 4. Intact + E2 | 9 | 0.05 + 0.01 | 30 |
| 5. Castrate + E2 | 6 | 0.04 + 0.01 | 9 |
| 6. Castrate + E2 + T | 7 | 0.59 + 0.06** | 13 |

N = Number of rats in each treatment group.
*p < 0.05 when compared with all other treatment groups.
**p < 0.05 when compared with Intact + E2, Castrate and Castrate + E2 treatment groups.

EXAMPLES

Animals and Gonadectomy: Male Charles River rats weighing approximately 250 g were purchased from the Wilmington, Mass. colony and were maintained in an AAALAC accredited vivarium for 1 week prior to gonadectomy. All animal procedures were approved by the University of Florida Animal Care and Use Committee. Bilateral gonadectomy was performed under methoxyllurane (Metophane® Pitman Moore, Crossings, N.J.) inhalant anesthesia 7 days prior to MCA occlusion.

Steroid Treatments: 17β-estradiol was packed into 5 mm long Silastic® tubes and testosterone was packed into 10 mm long silastic tubes that were closed on either end with Silastic Medical Adhesive® (Dow-Corning). Sham (empty) pellets were similarly prepared. All pellets were washed with methanol to remove the steroid adhering to the outside of the tubes. Subsequently, pellets were washed in physiological saline, a procedure that assures first order in vivo release of estradiol to achieve physiologically relevant concentrations [M. Singh, et al., *Brain Res.*, Vol. 644, (1994), pp. 305–312]. The pellets were implanted subcutaneously (sc) at the time of castration (1 week prior to the MCA occlusion).

Testosterone Assay: The blood from rats for radioimmunoassay (RIA) of testosterone was collected in heparinized tubes by intracardiac puncture just before sacrifice. The plasma was separated by centrifugation and stored at 80° C. until RIA. Coat-A-Count RIA kit was purchased from Diagnostics Products Corporation, Los Angeles, Calif. The tracer had high specific activity with approximately 30 to 40% maximum binding. The antiserum used was highly specific for testosterone with little cross reactivity to other compounds. The Coat-A-Count total testosterone assay had a broad reportable range of 4 to 1600 ng/dl, 50 μl of the same was used in duplicate tubes for RIA. The concentration of the unknown samples was read from the standard calibration curve whose correlation coefficient was 0.9989.

Middle Cerebral Artery Occlusion: At 7 days after gonadectomy and steroid implantation, animals were anesthetized with ketamine (60 mg/kg, ip) and zylazine (10 mg/kg, ip). During surgery, rectal temperature was maintained between 36.5 and 37.0° C. by a heating lamp. During an operating microscope, the left carotid artery was exposed through a midline incision of the neck. The sternohyloid, digastric (posterior belly) and the omohyloid muscles were divided and retracted. Then the greater hom of the hyloid bone was removed for exposure of the distal external carotid artery (ECA). The common carotid artery (CCA) was dissected from the vagus nerve and the ECA and its branches (occipital and superior thyroid arteries) were dissected distally. The internal carotid artery (ICA) was carefully separated from the vagus and glossopharyngeal nerves just below the ECA. Near the base of the skull, the ICA has an extracranial branch, the pterygopalatine artery. Beyond this bifurcation, the ICA enters the cranium medially. After the arteries and their branches were dissected, the distal ECA and its branches, the CCA and the Pterygopalatine arteries were cauterized completely. The ECA and the occipital arteries were cut, then a microvascular clip was placed on the internal carotid artery (ICA) near the base of the skull.

The tip of 2.5 cm long 3-0 monofilment nylon suture was heated to create a globule for easy movement and blockade of the lumen of the vessel. The suture was introduced into the ECA lumen through a puncture and was gently advanced to the distal ICA until it reached the clipped position. The microvascular slip was then removed and the suture was inserted until resistance was felt. The distance between the CCA bifurcation and the resistive point was 1.8 cm. The resistance indicated that the suture had passed the middle cerebral artery origin and reached the proximal segment of the anterior cerebral artery. The operative procedure was completed with 10 min. with minimal blood loss. After 40 minutes of occlusion time, the suture was withdrawn from the ICA and the distal ICA was immediately cauterized.

Quantitation of Mortality and Ischernic Area: Animals that survived until the scheduled sacrifice time (24 hours after MCA occlusion) were killed by decapitation. Prior to sacrifice, cardiac puncture was used to obtain blood samples for subsequent assessment of plasma testosterone concentration. Brains were removed 24 hours after MCA occlusion and placed in a metallic brain matrix (ASI Instruments, Inc., Warren, Mich.) for slicing. Coronal sections 2 mm thick were made at 5, 7, 9, 11 and 13 mm posterior to the olfactory bulb. The slices were incubated for 30 minutes in a 2% solution of 2, 3, 5 triphenyltetrazolium chloride (Sigma Chemical Corp., St. Louis, Mo.) in physiological saline at 37° C. Stained slices were photographed and subsequently imaged using a McIntosh Quatra 800 computer, equipped with an Image 1.47 software program for the assessment of the ischemic area of the lesion. The area of the entire sliced brain was outlined and quantified; and, then, the ischemic area was outlined and quantified. The ratio of ischemic area to total brain area was calculated to give the percent ischemic area for each brain slice. The ischemic area in each brain slice was averaged for each animal and the number was recorded. This was done for each animal in each group to produce the mean ischemic area. These images and calculated area of ischemia were stored for later retrieval and data reduction.

Statistical Evaluation of Data: The significance of differences in lesion size among the 6 treatment groups was determined by ANOVA and the Fischer's test was used for the post hoc analysis. $P<0.5$ was considered significant. The correlation between testosterone and the lesion size was analyzed by regression analysis. The significance of the mortality of the rates prior to sacrifice was analyzed by Chi Square analysis.

Figure 2:
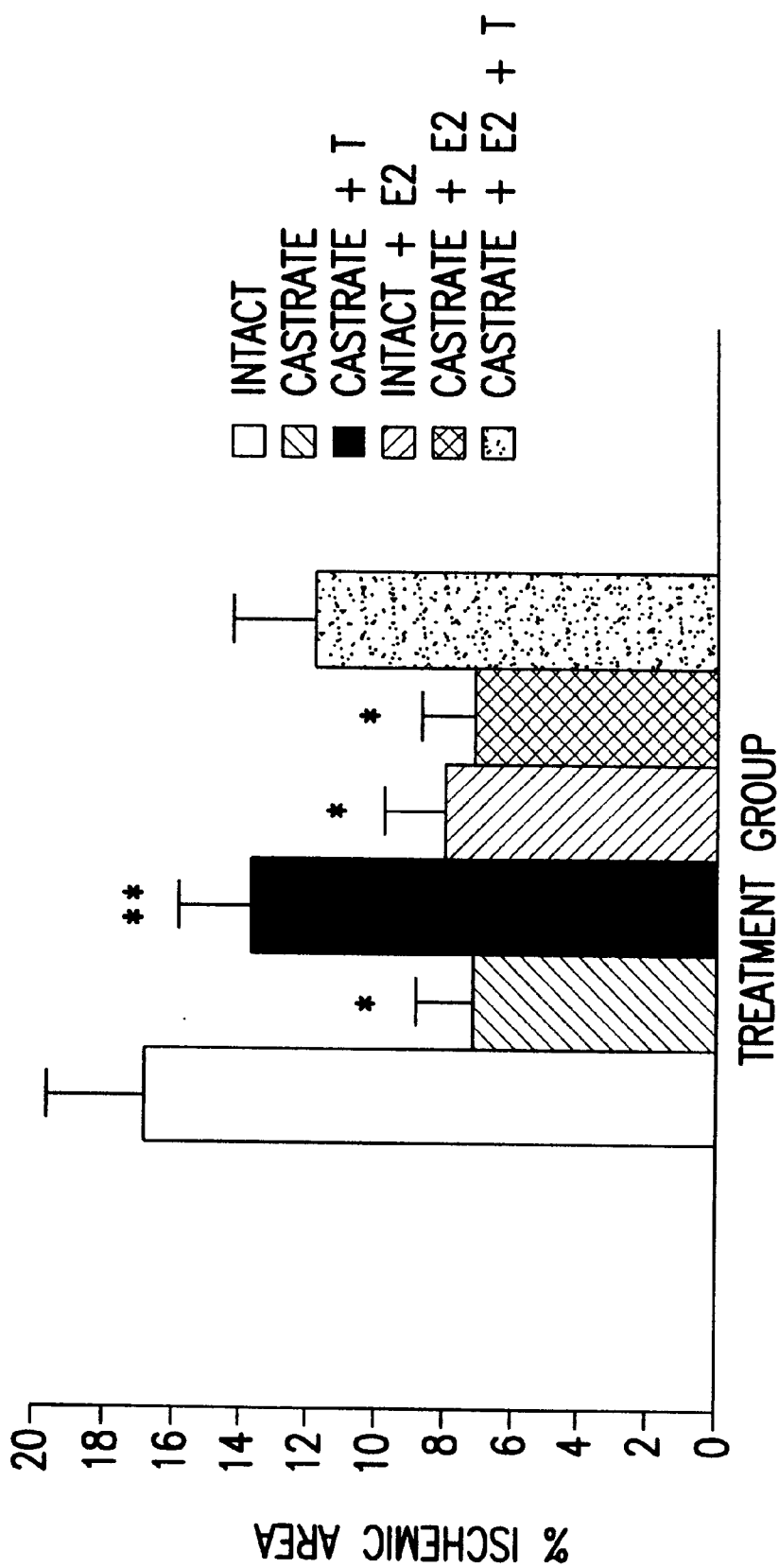
FIG. 2 shows the effects of endocrine manipulation on mean percent ischemic area (mean±SEM) in male rats. * indicates p<0.05 versus Intact. ** indicates p<0.05 versus Castrate and Castrate+E2 groups. Data is presented from intact rats, castrated rats, castrated rats treated with testosterone, intact rats treated with estradiol, castrated rats treated with estrogen and castrated rats treated with estradiol and testosterone.

The effects of castration and testosterone replacement on ischemic damage following MCA occlusion is shown in FIG. 1. Intact rats showed the expected rostral to caudal extent of ischemic damage with peak ischemic lesions observed at 7 and 9 mm caudal to the olfactory bulb. Lesion size was small at more rostral and caudal brain sections. The MCA occlusion lesion occupies the expected brain regions, i.e., the frontal and parietal cortex and basal ganglia, supplied by the MCA [S. A. Menzies, et al, *Neurosurgery*, Vol. 31, (1992), pp. 100–106]. Castration of adult male rats reduced ischemic lesion size in each section evaluated (FIG. 1) and reduced the overall mean ischemic are from 17±3% in intact rates to 8±2% in castrate rates (FIG. 2). Testosterone replacement of castrate rats increased lesion size in all sections evaluated (FIG. 1) and increased overall mean ischemic area to 14±2% (FIG. 2).

Estrogens are neuroprotective against MCA occlusion-induced ischemic brain damage in female rats (U.S. Ser. No. 08/749,703 incorporated by reference). Here, we evaluated the effects of estrogen treatment in males. Treatment of intact male rats with 17β-estradiol reduced overall mean ischemic area from 17±3% to 8±2% (FIG. 2). Treatment of castrated males with estradiol did not change the already reduced size of the MCA occlusion-induced lesion (FIG. 2). Simultaneous treatment with both testosterone and estradiol in castrated rats resulted in an ischemic lesion of 12±2%, intermediate between that of castrate +T(14±2%) and castrate +T(14±2%) and castrate +E2(7±2%) (FIG. 2).

Castrate +E2 treatment profoundly reduced plasma testosterone concentration from 1.556±0.409 nglml in intact male rats to 0.069±0.029 ng/ml and 0.054±0.010 ng/ml in castrate and intact +E2-treated animals, respectively (Table 1). Testosterone replacement in castrate or castrate +E2 rats increased plasma testosterone concentration to 0.668±0.067 ng/ml and 0.590±0.055 ng/ml, respectively (Table 1).

Figure 3:
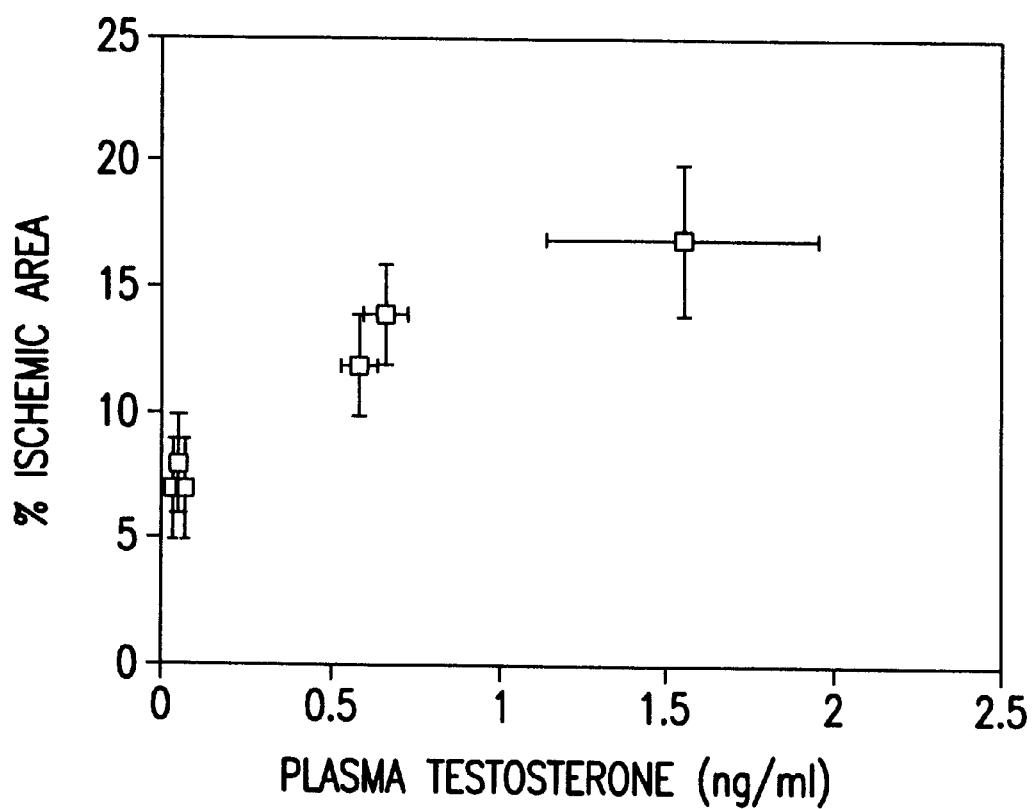
FIG. 3 shows the relationship between plasma testosterone concentration and mean percent ischemic area in male rats. Depicted are the mean ±SEM for both plasma testosterone concentration and percent mean ischemic area for the six treatment groups evaluated. The $r^2$ value for the relationship is 0.922.

We conducted an analysis of covariance to assess the relationship between plasma testosterone and overall mean percent ischemic area (FIG. 3). A $r^2$ of 0.922 was observed when ischemic area was analyzed on the basis of plasma testosterone concentrations.

Mortality (deaths prior to the scheduled 24 hour sacrifice time) was high in the intact group (46%) and the intact +E2 group (30%), but was low (9–15%) in all castrate groups, regardless of their hormone replacement (Table 1).

We claim:
1. A method of conferring neuroprotection on a population of cells in a subject, comprising:
   (a) providing an effective dose of a testosterone inhibitor, wherein the testosterone inhibitor is selected from the group consisting of: a GnRH release inhibitor other than a GnRH antagonist, non-steroidal aniti-androgen, androgen synthesis inhibitor, a GnRH peptide analog, a luteinising hormone releasing hormone agonist and a 5-alpha-reductase inhibitor in a pharmaceutical formulation, wherein the testosterone inhibitor does not include either four ring cyclopentano phenanthrene compounds or estrogen compounds wherein estrogen compounds include estrogen agonists; and (b) administering the inhibitor to the subject so as to confer neuroprotection.

2. A method according to claim 1, wherein the subject is a male subject.

3. A method according to claim 1, wherein step (b) further comprises administering the inhibitor by a route selected from the group consisting of oral, intramuscular, transdermal, buccal, intravenous and subcutaneous.

4. A method of conferring neuroprotection on a population of cells in a subject, comprising:

(a) providing a mixture containing a plurality of non-estrogen testosterone inhibitors at an effective dose and in a pharmaceutical formulation, wherein the testosterone inhibitor is selected from the group consisting of a GRH release inhibitor other than a GnRH antagonist, non-steroidal anti-androgen, androgen synthesis inhibitor, a GnRH peptide analog, a luteinising hormone releasing hormone agonist and a 5-alpha-reductase inhibitor in a pharmaceutical formulation, wherein the testosterone inhibitor does not include either four ring cyclopentano phenanthrene compounds or estrogen compounds wherein estrogen compounds include estrogen agonists; and (b) administering the inhibitor to the subject so as to confer neuroprotection.

5. A method of treating a neurodegenerative disorder in a subject, comprising:

(a) providing an effective dose of a non-estrogen testosterone inhibitor in a pharmaceutical formulation wherein the testosterone inhibitor is selected from the group consisting of a GnRH release inhibitor other than a GnRH antagonist, non-steroidal anti-androgen, androgen synthesis inhibitor, a GnRH peptide analog, a luteinising hormone releasing hormone agonist and a 5-alpha-reductase inhibitor in a pharmaceutical formulation, wherein the testosterone inhibitor does not include either four ring cyclopentanophenanthrene compounds or estrogen compounds wherein estrogen compounds include estrogen agonists; and (b) administering the formulation to the subject so as to retard the adverse effects of the disorder.

* * * * *

UNITED STATES PATENT AND TRADEMARK OFFICE
CERTIFICATE OF CORRECTION

PATENT NO. : 6,172,088
DATED : January 9, 2001
INVENTOR(S) : Simpkins et al.

It is certified that error appears in the above-identified patent and that said Letters Patent are hereby corrected as shown below:

Column 8, line 66, change "aniti-androgen" to --anti-androgen--
Column 9, line 21, change "GRH" to -GnRH--

In the abstract, replacethe entire paragraph beginning with "Androgens and their derivates ..." and ending with "non androgen-dependent malign neoplasia" with the following paragraph.

--Methods are provided of conferring neuroprotection on a population of cells or treating a neurodegenerative disease in a subject. The methods include providing an effective dose of a testosterone inhibitor or a mixture of a plurality of testosterone inhibitors and administering the inhibitor(s) to the cells. The testosterone inhibitor may be selected from the group consisting a GnRH release inhibitor other than a GnRH antagonist, a non-steroidal anti-androgen, an androgen synthesis inhibitor, a GnRH peptide analog, a luteinising hormone releasing hormone agonist and a 5-alpha-reductase inhibitor, wherein the testosterone inhibitor does not include either four ring cyclopentanophenanthrene compounds or estrogen compounds wherein estrogen compound includes estrogen agonists--

Signed and Sealed this

Twenty-ninth Day of May, 2001

*Attest:*

NICHOLAS P. GODICI

*Attesting Officer*   Acting Director of the United States Patent and Trademark Office

UNITED STATES PATENT AND TRADEMARK OFFICE
Certificate

Patent No. 6,172,088 B1                                                                                         Patented: January 9, 2001

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: James W. Simpkins, Gainesville, FL; Katherine Gordon, Winchester, MA; and Robert Leonard, Swampscott, MA.

Signed and Sealed this Sixth Day of July 2004.

JAMES O. WILSON
*Supervisory Patent Examiner*
Art Unit 1623